US006203503B1

(12) United States Patent
Kelly et al.

(10) Patent No.: US 6,203,503 B1
(45) **Date of Patent: *Mar. 20, 2001**

(54) COLLECTION CONTAINER ASSEMBLY

(75) Inventors: Karin E. Kelly, Los Angeles, CA (US); Ray Wasek, Jamesburg; Gary R. Henniger, Wayne, both of NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/306,930

(22) Filed: May 7, 1999

Related U.S. Application Data

(63) Continuation of application No. 08/928,817, filed on Sep. 12, 1997, now Pat. No. 5,938,621.

(51) Int. Cl.[7] .................................................... A61B 5/00
(52) U.S. Cl. .................................................... 600/573
(58) Field of Search .................................... 600/573–584; 73/863.32

(56) References Cited

U.S. PATENT DOCUMENTS

| | | | | |
|---|---|---|---|---|
| 3,645,252 | * | 2/1972 | Gilford | 600/575 |
| 4,469,482 | * | 9/1984 | Lissenbuy et al. | 600/578 |
| 5,054,498 | * | 10/1991 | Melet | 600/576 |
| 5,086,784 | * | 2/1992 | Levine et al. | 600/584 |
| 5,181,523 | * | 1/1993 | Wendelborn | 600/577 |
| 5,277,198 | * | 1/1994 | Kanner et al. | 600/578 |
| 5,938,621 | * | 8/1999 | Kelly et al. | 600/573 |

* cited by examiner

*Primary Examiner*—Max Hindenburg
(74) *Attorney, Agent, or Firm*—Nanette S. Thomas, Esq.

(57) ABSTRACT

The present invention is a collection container assembly comprising a container having an inert plug inside the bottom end of the container and wherein the external dimensions of the container are substantially the same as a standard-sized blood collection tube but with a reduced internal volume.

8 Claims, 4 Drawing Sheets

COLLECTION CONTAINER ASSEMBLY

This application is a continuation of Ser. No. 08/928,817 filed Sep. 12, 1997, now U.S. Pat. No. 5,938,621.

BACKGROUND OF THE INVENTION

1. Field of the Invention

This invention relates to a specimen collection container assembly and more particularly to a collection container for collecting biological fluid specimens where a small quantity of fluid may be collected and retained in the container while maintaining a container size sufficient to be easily accommodated and/or compatible with standard clinical equipment and instrumentation.

2. Description of Related Art

Blood samples and other biological fluid specimens are routinely taken and analyzed in hospital and clinical situations for various medical purposes. Collection, handling and testing of these samples typically requires the use of various medical testing instruments. As the blood and fluid specimens are usually collected in a standard sized collection tube, the medical instruments used to test the samples are designed to accommodate these standard sized collection tubes.

Conventional blood collection tubes used in most clinical situations are elongated cylindrical containers having one end closed by a semi-spherical or rounded portion and an opposed open end. The open end may be sealed by a resilient cap or stopper. The tube defines a collection interior which collects and holds the blood sample. The most common size of these blood collection tubes are designed to accommodate approximately 10 ml of blood or other biological fluid samples. Illustrative of such blood collection tubes is the VACUTAINER® brand blood collection tube sold by Becton, Dickinson and Company, 1 Becton Drive, Franklin Lakes, N.J. (registered trademark of Becton, Dickinson and Company).

A phlebotomist or other medical technician typically obtains a specimen of the patient's blood in the tube by techniques well known in the art. The tube is then appropriately labeled and transferred from the site of collection to a laboratory or other location where the contents of the tube are analyzed. During collection and analysis the tube may be supported by various medical instruments. The plasma or serum derived therefrom is processed and analyzed either manually, semi-automatically or automatically. In some cases, the specimen must first be dispensed from the collection tube to a sample test tube or cuvette.

In certain situations it is only necessary to obtain a small quantity of blood or other biological fluid specimens. These situations may include pediatric, or geriatric patients and other instances where large blood samples are not required. Small quantities of blood cannot be easily collected in standard collection tubes as described above because the sample level in such containers would not be adequate for retrieval prior to analysis. Such small quantities of fluids also have a tendency to significantly evaporate when stored in larger containers, thus concentrating the chemical and enzymatic constituents therein. This may result in erroneous analytical results and could possibly affect the diagnosis and treatment given to the patient. Therefore, it is desirable to employ small-volume containers which substantially inhibit evaporation for the storage and delivery of minute fluid samples in the laboratory.

Various specimen containers such as those incorporating a "false bottom" have been proposed to achieve decreased volume capacity in conjunction with standard external dimensions. However, these various specimen containers are not compatible with standard clinical equipment and instrumentation due to their design. In particular, these specimen containers have false bottoms with a generally flat, planar bottom end and a circular shaped opening.

Other specimen containers include partial-draw tubes which have standard external dimensions with partial evacuation so that blood fills only a portion of the internal volume. However, partial-draw tubes exhibit a reduction in the draw rate of a sample which reduces the collection efficiency of such tubes. In addition, partial-draw tubes may result in an inconsistent fill volume which may alter test results. Furthermore, it is difficult to determine accurate sample quantities with such partial-draw tubes because the slow rate of sample draw is not consistently measurable.

In clinical use, it is desirable for such specimen collection containers to have rounded bottom configurations that closely simulate a standard-sized blood collection tube configuration instead of planar bottoms. Rounded bottom configurations facilitate compatibility with clinical equipment and instrumentation.

Therefore there is a need to provide a specimen collection container assembly for collecting blood samples and other biological fluid specimens of relatively small volumes where the assembly may be accommodated and/or compatible with standard clinical equipment and/or instrumentation and where the integrity of the sample and specimens are maintained during draw, storage and transport.

SUMMARY OF THE INVENTION

The present invention is a collection assembly comprising a container. The container preferably comprises an open top portion, a bottom portion and a sidewall extending from the open top portion to the bottom portion. The bottom portion comprises a closed bottom end. The assembly further comprises an inert plug permanently positioned within the interior of the container near the closed bottom end. Optionally, the assembly may further comprise a closure at the open top portion of the container.

Most preferably, the inert plug occupies space within the container so as to reduce the interior volume of the container thereby creating a false bottom to the container. Most preferably, the inert plug is non-removable within the container.

The inert plug of the container provides a false bottom effect to the assembly and the extension provides a means for allowing the container to be modified so as to be compatible with standard clinical equipment and instrumentation The inert plug may be the same or different material than the container. The inert plug comprises a top portion, a bottom portion, and a solid column extending from the top portion to the bottom portion.

The inert plug may be the same or different material than the container and may be integral with the container or may be a discrete member. Additionally, the top of the inert plug may be arcuate in shape to provide a volume for the container whereby the top portion of the inert plug would provide a partially rounded internal bottom portion to the container.

In addition, the assembly may further comprise a closure such as a cap or a stopper at the open end of the container.

Preferably, the external dimensions of the assembly are about the same as a standard-sized or full draw blood collection container assembly. A standard-sized or full draw blood collection container has an outer diameter of about 13 to about 16 millimeters, a length of about 75 to about 100 millimeters and an integral volume of about 6 to about 10 millilters.

Most preferably, the assembly of the present invention can be either evacuated or non-evacuated. Desirably, the assembly is made from polyethylene terephthalate, polypropylene, polyethylene, polyethylene napthalate polyvinyl chloride or copolymers thereof.

An advantage of the assembly of the present invention is that it provides a full-draw blood collection container assembly having a reduced internal volume but with external dimensions about the same as a standard-sized blood collection container assembly. In addition, the assembly of the present invention has a standard draw rate as compared to partial draw rate tubes.

A further advantage of the assembly of the present invention is that it provides a specimen collection container which is universally compatible with various clinical equipment and instrumentation.

The assembly of the present invention may be easily handled by equipment configured to handle standard-sized blood collection tubes having standard external dimensions.

Most notably, is that the assembly of the present invention provides a blood collection container having full draw external dimensions but with a reduced internal volume as compared to standard-sized full draw blood collection tubes or standard-sized partial draw blood collection tubes.

The assembly of the present invention therefore addresses the need for a filldraw low-volume blood collection container assembly that presents the external dimensions of a standard-sized blood collection tube.

The assembly of the present invention may be used to reliably collect small samples of blood or biological fluids and to maintain the integrity of the samples during storage and transport as compared to using standard-sized blood collection tubes. In addition, the assembly of the present invention can also be accommodated by standard-sized blood collection, transportation, storage, and diagnostic equipment. Furthermore, the assembly of the present invention may be used to reliably collect small samples of blood or biological fluids without being under partial pressure.

Most notably, is that the assembly of the present invention provides a rounded bottom configuration that is substantially the same as a standard-sized blood collection tube with a fully rounded bottom. This particular feature in conjunction with all of the features of the container, distinguishes it from the specimen containers that have flat planar bottoms and from partial draw blood collection tubes.

The assembly of the present invention is also compatible with existing instrumentation, labels, and bar code readers and obviates the need for new instrumentation and handling devices or procedures that would be required for smaller or varying sized tubes or tubes with flat planar bottoms.

DETAILED DESCRIPTION

The present invention may be embodied in other specific forms and is not limited to any specific embodiment described in detail which is merely exemplary. Various other modifications will be apparent to and readily made by those skilled in the art without departing from the scope and spirit of the invention. The scope of the invention will be measured by the appended claims and their equivalents.

Figure 1:
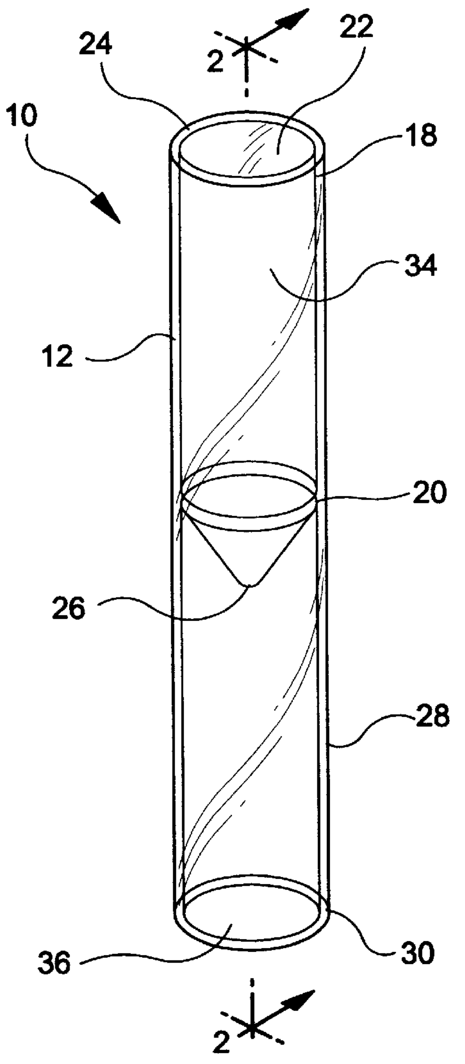
FIG-1 PRIOR ART
FIG. 1 is a perspective view of a false bottom specimen tube of the prior art.
Figure 2:
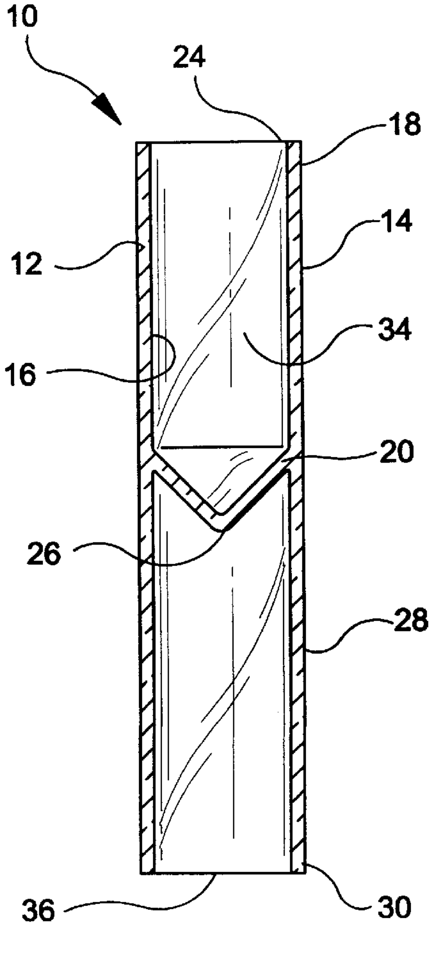
FIG-2 PRIOR ART
FIG. 2 is a longitudinal sectional view of the tube of FIG. 1 taken along line 2—2 thereof.

Referring to the drawings in which like reference characters refer to like parts throughout the several views thereof, FIGS. 1 and 2 show a false bottom specimen container 10 of the prior art, having a sidewall 12 having an outer surface 14 and an inner surface 16. Sidewall 12 extends from an upper portion 18 to a lower portion 20. Upper portion 18 includes an open end 22 and a rim 24. Lower portion 20 comprises a closed bottom end 26. An annular skirt 28 extends from lower portion 20 and outer surface 14 to a flat planar bottom end 30 to define an open false bottom area 36. Interior volume 34 extends between rim 24 and closed bottom end 26.

Figure 3:
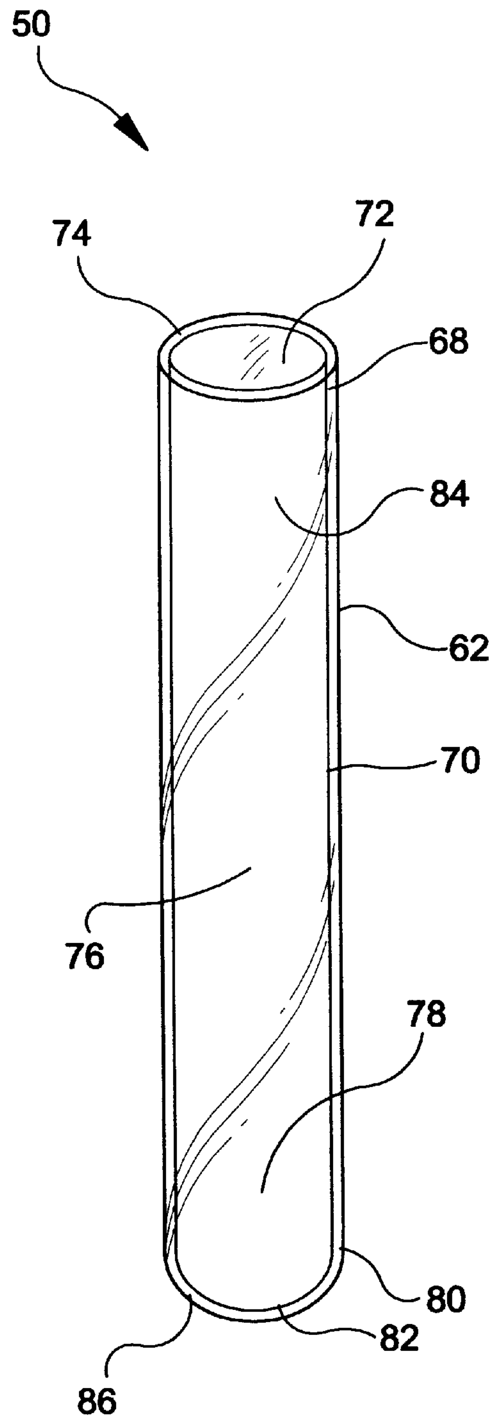
FIG. 3 is a perspective view of the assembly of the present invention without the inert plug.
Figure 5:
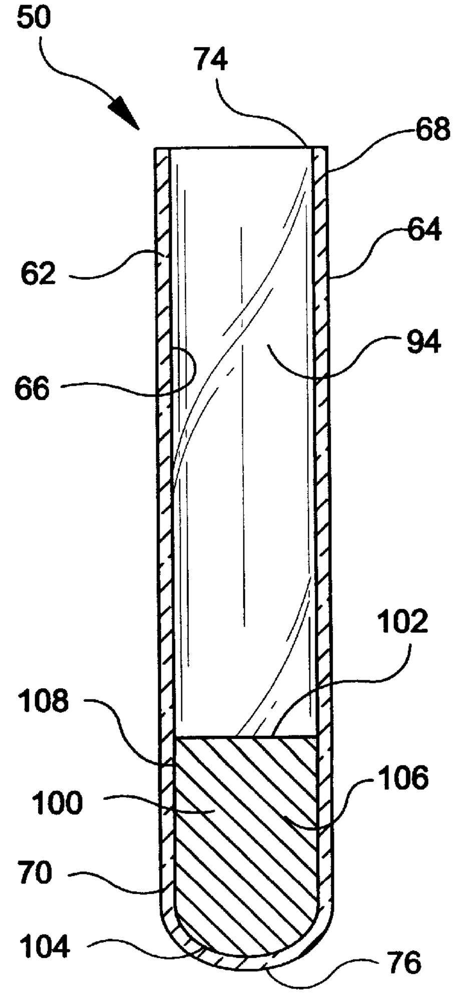
FIG. 5 is a longitudinal sectional view of the assembly of FIG. 4 taken along line 5—5 thereof.

Referring to the drawings in which like reference characters refer to like parts throughout the several views thereof, FIGS. 3 and 5 show the preferred embodiment of the present invention, assembly 50. Assembly 50 is a false bottom specimen container, having a sidewall 62 having an outer surface 64 and an inner surface 66. Sidewall 62 extends from an upper portion 68 to a lower portion 70. Upper portion 68 includes an open end 72 and a rim 74. Lower portion 70 comprises a dosed bottom end 76 with dosed bottom interior area 78. In addition, an inert plug 100 is located in closed bottom interior area 78.

Inert plug 100 includes a top portion 102, a bottom portion 104 and a column 106 extending from the top portion to the bottom portion. Column 106 is solid therefore comprising a sidewall 108. Top portion 102 is shown as a substantially flat or planar surface however it is within purview of this invention that top portion 102 may be any shape such as conical, concave, convex, arcuate, or semi-spherical. Bottom portion 104 is shown having the same shape as closed bottom interior area 78, which is rounded or substantially semi-spherical in shape. However it is within purview of this invention that bottom portion 104 may be substantially flat, planar, conical, concave, convex or arcuate.

Inert plug 100 is most preferably made of a biologically inert material such as silicone rubber, polypropylene, polyester gel, polyethylene terephthalate, polyethylene or epoxy, that will not have any effect on fluids collected in the container. Inert plug 100 is most preferably fixed with the closed bottom interior is area of the container so that it will not travel when the container is subjected to stress or process handling situations, such as transport and centrifugation.

Additionally, inert plug 100 may be integral with sidewall 62 or may be a discrete member. Preferably inert plug 100 is integrally formed with sidewall 62.

Most preferably, inert plug 100 may be formed of a high density filler in the form of a gel. Such a gel may be a polyester or similar material that has a sufficient density to resist moving within the container when the container is subjected to stress or process handling situations, such as transport and centrifugation. In addition the gel must exhibit and maintain an even weight distribution during centrifugation.

Alternatively, inert plug 100 may be adhesively fixed to the inner surface of the sidewall of the container or inert plug 100 may be formed wherein column 106 has a larger diameter than the inner diameter of the container so that the inert plug may be held in place by an interference fit.

Alternatively, inert plug 100 may be delivered to the inside area of the container as a liquid viscous state which subsequently cures or hardens into a solid and an interference fit then exists between the plug and the inner surface of the sidewall of the container.

In addition to providing a false bottom to a container as well as a reduced volume to a container, inert plug 100 may also serve as a visual indicator for things such as product differentiation or distinction for tube type, draw volume, shelf life, additive type or identification with various instrument analyzers for specific clinical use such as hematology, chemistry, coagulation, etc. The visual indicator may be that the plug is a certain color or color pattern.

Inert plug 100 may be positioned at any point below rim 74 thus providing a variable interior volume 94 between rim 74 and top portion 102 of the inert plug. Most preferably, top portion 102 of the inert plug may be arcuate in shape to provide at least a partially rounded false bottom surface for interior volume 94.

Inert plug 100 provides means for converting the assembly to substantially the same external dimensions as a standard-sized blood collection tube.

Figure 4:
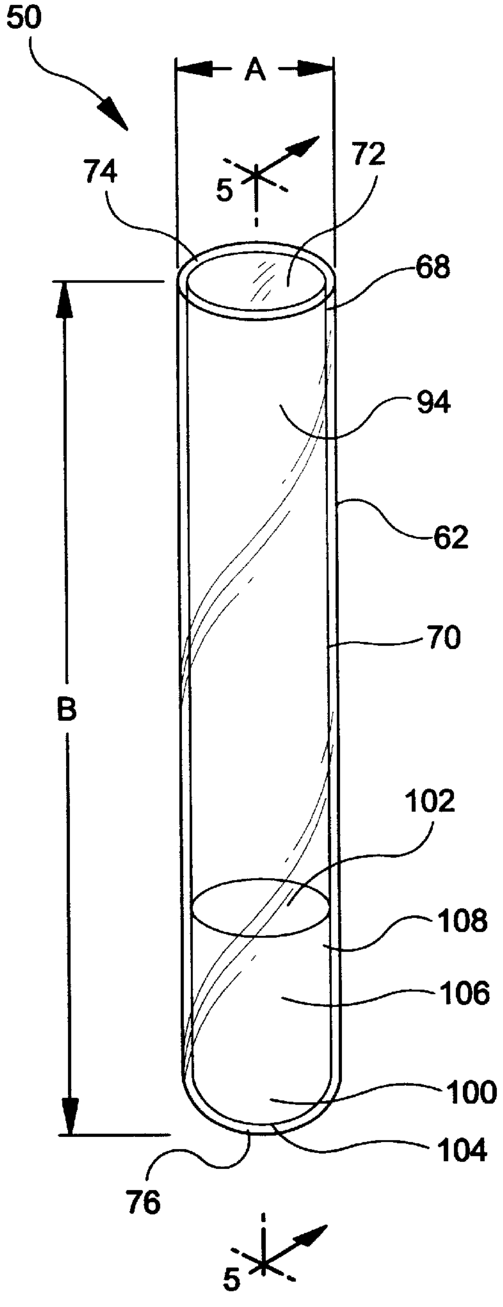
FIG. 4 is a perspective view of the assembly of the present invention with the inert plug.

As shown in FIG. 4, assembly 50 has an outer diameter A of about 13 millimeters, a length B of about 75 millimeters, as measured from rim 74 to closed bottom end 76 and an interior volume 94 of about 1 to 3 milliliters, as measured from rim 74 to top portion 102 of inert plug 100. It is within the purview of this invention that assembly 50 may have an outer diameter of about 13 to about 16 millimeters, a length of about 75 to about 100 millimeters and an interior volume of about 1 to about 3 milliliters.

Figure 6:
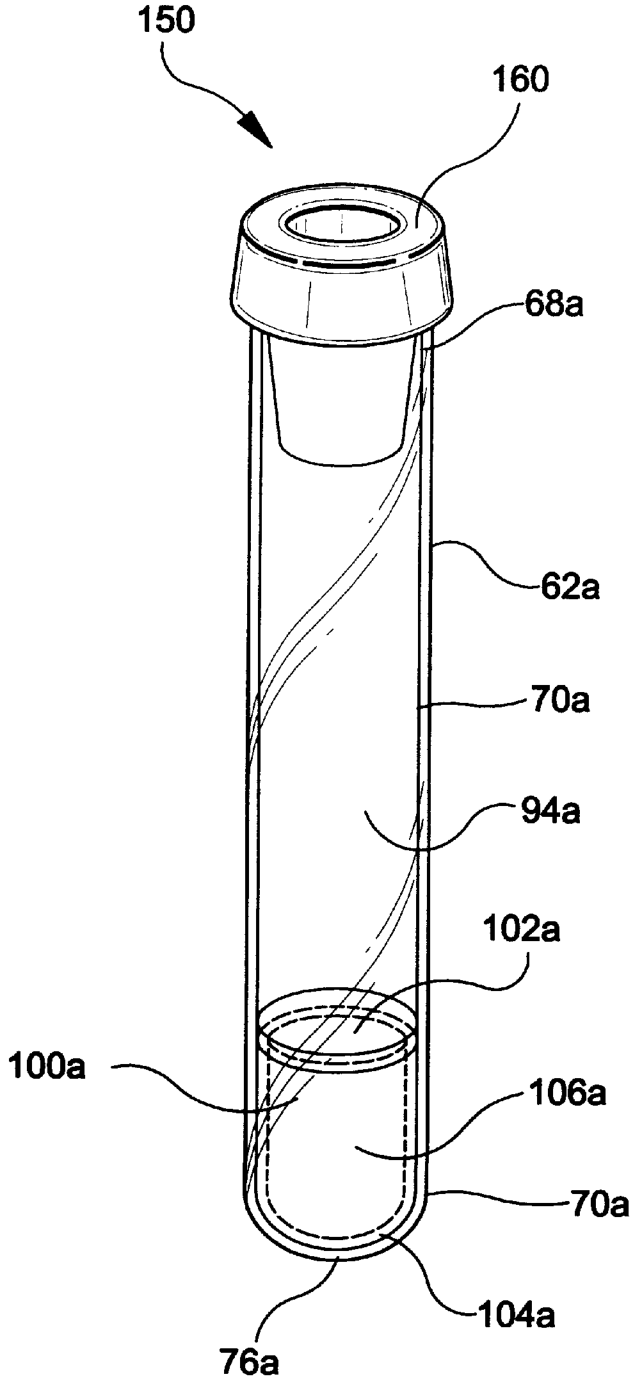
FIG. 6 is a perspective view of an alternate embodiment of the present invention.

The invention, as shown in FIG. 6 includes many components which are substantially identical to the components of FIGS. 4–5. Accordingly, similar components performing similar functions will be numbered identically to those components of FIGS. 4–5, except that a suffix “a” will be used to identify the similar components in FIGS. 6.

As illustrated in FIG. 6, a further embodiment of the invention is assembly 150 which includes a closure 160.

The embodiment of FIG. 6 may be evacuated or non-evacuated. When assembly 150 is evacuated, interior volume **94*a* is typically maintained at a lower-than-atmospheric internal pressure so that when a blood collection probe penetrates through the closure placing interior volume 94*a* in communication with the circulatory system of a patient, the lower-than-atmospheric pressure of interior volume 94*a* will draw blood from the patient into the tube. Assembly 150 may be described as a full-draw blood collection tube because the internal pressure of interior volume 94*a* is low enough to draw a volume of blood substantially equal to the volume of interior volume 94*a***.

What is claimed is:

1. A collection assembly comprising:

a container comprising a top portion, a closed bottom portion, a sidewall extending from said top portion to said bottom portion, and an inert plug permanently fixed in said bottom portion of said container by an interference fit with said sidewall of said container comprising a top portion, a bottom portion, and a column extending between said top portion and said bottom portion of said inert plug.

2. The assembly of claim 1, wherein said top portion of said inert plug is arcuate in shape.

3. The assembly of claim 1, further comprising a closure.

4. The assembly of claim 1, wherein said assembly comprises an outer diameter, a length and an internal volume, wherein said outer diameter is about 13 to about 16 millimeters, said length is about 75 to about 100 millimeters, and said interior volume is about 1 to about 3 milliliters.

5. The assembly of claim 1, wherein said inert plug is made of a biologically inert material.

6. The assembly of claim 5, wherein said biologically inert material is selected from the group consisting of silicone rubber, polypropylene, polyester gel, polyethylene terephthalate, polyethylene or epoxy.

7. The assembly of claim 1, wherein said inert plug is a visual indicator.

8. The assembly of claim 7, wherein said inert plug is a color or color pattern.

* * * * *